(12) United States Patent
Zimmon

(10) Patent No.: US 7,445,603 B2
(45) Date of Patent: Nov. 4, 2008

(54) APPARATUS FOR REMOVABLE DISTAL INTERNAL CASSETTE FOR IN SITU FIXATION AND SPECIMEN PROCESSING WITH SERIAL COLLECTION AND STORAGE OF BIOPSY SPECIMENS

(75) Inventor: David Zimmon, Port Washington, NY (US)

(73) Assignee: ZKZ Science Corp., Port Washington, NY (US)

( * ) Notice: Subject to any disclaimer, the term of this patent is extended or adjusted under 35 U.S.C. 154(b) by 0 days.

(21) Appl. No.: 10/843,777

(22) Filed: May 12, 2004

(65) Prior Publication Data

US 2005/0256424 A1  Nov. 17, 2005

(51) Int. Cl.
*A61B 10/00* (2006.01)
*A61B 17/00* (2006.01)

(52) U.S. Cl. ........................................ 600/564; 606/205

(58) Field of Classification Search .................. 600/562, 600/564–67; 606/167, 170, 205–209
See application file for complete search history.

(56) References Cited

U.S. PATENT DOCUMENTS

| | | | |
|---|---|---|---|
| 5,490,859 A * | 2/1996 | Mische et al. ................ 606/159 |
| 5,665,100 A * | 9/1997 | Yoon ........................... 606/170 |
| 5,685,320 A | 11/1997 | Zimmon | |
| 5,779,648 A * | 7/1998 | Banik et al. .................. 600/567 |
| 5,782,747 A | 7/1998 | Zimmon | |
| 5,871,453 A * | 2/1999 | Banik et al. .................. 600/564 |
| 6,053,877 A * | 4/2000 | Banik et al. .................. 600/566 |
| 6,071,248 A | 6/2000 | Zimmon | |
| 6,083,150 A * | 7/2000 | Aznoian et al. .............. 600/564 |
| 6,139,508 A * | 10/2000 | Simpson et al. .............. 600/564 |
| 6,322,522 B1 | 11/2001 | Zimmon | |
| 6,468,227 B2 | 10/2002 | Zimmon | |
| 6,632,182 B1 * | 10/2003 | Treat ........................... 600/564 |
| 2002/0138021 A1* | 9/2002 | Pflueger ....................... 600/565 |
| 2003/0086830 A1* | 5/2003 | Haywood et al. ............ 422/102 |
| 2004/0030263 A1* | 2/2004 | Dubrul et al. ................ 600/565 |

* cited by examiner

*Primary Examiner*—Max Hindenburg
*Assistant Examiner*—Jonathan M Foreman
(74) *Attorney, Agent, or Firm*—Collard & Roe, P.C.

(57) ABSTRACT

An apparatus for performing a medical procedure comprises an elongated flexible member having an aperture extending longitudinally therethrough and an actuator positioned within the aperture. There is a biopsy means connected to the distal end of the actuator for cutting and collecting biopsy specimens and a removable distal storage and collection chamber connected to the elongated flexible member for receiving biopsy specimens cut and collected by the biopsy means. The removable storage and collection chamber is a means for immediate contact of the collected biopsy specimens with fixatives or reagents. The distal cassette is separable from the flexible member and can be sealed by a cap positionable over the storage and collection cassette for storage, in situ fixation and processing or later processing and analysis of biopsy specimens collected by the biopsy means in the order of collection.

8 Claims, 2 Drawing Sheets

APPARATUS FOR REMOVABLE DISTAL INTERNAL CASSETTE FOR IN SITU FIXATION AND SPECIMEN PROCESSING WITH SERIAL COLLECTION AND STORAGE OF BIOPSY SPECIMENS

BACKGROUND OF THE INVENTION

1. Field of the Invention

The present invention relates to an apparatus for serial collection, storage and processing of biopsy specimens. The device cuts and captures a biopsy specimen with a closely defined size to permit serial entry into a removable distal storage cassette for in situ chemical, biological or genetic testing by immediately reacting with the biopsy specimens before metabolic changes, degradation or contamination can occur or for fixation, staining and other processing and analysis. The cassette may be optically transparent for physical analysis of the tissue without removal from the cassette after separation from the biopsy instrument. Prior to biopsy the open tube shaft with a side arm permits fluid sampling, irrigation, and injection of tissue stains or radiopaque contrast agents.

2. The Prior Art

It is often necessary to obtain tissue samples for examination from deep within structures. These samples can only be retrieved by catheterization methods using endoscopic or fluoroscopic control, or by blind palpation. The biopsy devices previously used for these techniques removed 1 to 4 specimens that were retrieved by removing the biopsy instrument from the patient, and placing the specimen in a container of fixative solution labeled with the biopsy site and patient identification. During this process of acquisition and collection minute specimens were frequently lost and are always contaminated by handling and passage through the endoscope instrument channel. Furthermore during acquisition the staff is exposed to potentially infectious human tissue and toxic fixatives.

The biopsies obtained in each pass were processed in a batch, since the minute pieces could not be easily separated. Multiple biopsy passes were required because of the limited storage capacity of the biopsy instruments and the need to identify the origin of each biopsy sites. Consequently, biopsies from different anatomic sites were handled separately, thus requiring considerable effort and expense. After each biopsy pass the biopsy(s) must be removed from the biopsy instrument and placed in a labeled fixative container. The biopsy instrument was washed to remove fixative and returned to the endoscopist for passage through the endoscope for the next biopsy. This prolonged the procedure and could cause it to fail, if the position of the biopsy instrument could not be reacquired during the repeated passes of the biopsy instrument through the endoscope. This complexity prolonged the endoscopic procedure and increased the quantity of sedative administered to the patient, risk and cost.

The containers for each patient were then transported to the laboratory where each container was serially opened and each specimen batch transferred to individual numbered cassettes that were recorded for later identification. The cassettes were then processed for examination. The processed specimens were then sliced, stained and mounted on labeled slides for microscopic examination. The specimens in each container must be processed and mounted on slides separately to maintain identification. This was particularly important when the distribution and extent of a cancer was being mapped to determine therapy and to prevent errors in reporting.

During this complex handling process, small specimens may be lost or damaged. At each stage of handling, the staff is exposed to infection from the biopsies and fixative. This is particularly true when the unfixed specimen is removed from the sharp biopsy instrument before fixation. The staff is also exposed to solvent vapor from the fixative at each transfer step of processing. The solvents may be allergenic or carcinogenic. This tedious, labor intensive process is expensive in staff required, time, equipment and laboratory space.

Specimens needed for chemical, biological or genetic testing require additional biopsies that must be handled separately. These specimens were contaminated by fluid and tissue in the track traversed to obtain the biopsies and within the channel of the endoscopic instrument. The delay in acquisition and contamination of the specimens limit the accuracy and reliability of the subsequent analysis. This disability may be severe when genetic or biological testing is needed.

The prior art described in the spring based multipurpose medical instrument in U.S. Pat. No. 5,782,747 to Zimmon, the disclosure of which is herein incorporated by reference, obviates the use of cumbersome metal shafts and coverings that occupy the space needed for specimen storage. Standard jaw fulcrum biopsy devices require a stiff shaft to prevent kinking and binding within the endoscope when the actuator cable(s) is pulled to close the biopsy jaws and then held to maintain jaw closure when removing the device and biopsy from the endoscope or access passage. The combined stiffness of the shaft and pull on the actuator cable(s) straightens the biopsy device and endoscope. This action moves the endoscope and biopsy device away from the biopsy site, limits maneuverability and prevents rapid serial biopsy of the target site. This stiffness and uncontrolled motion also risks trauma to the biopsy site and limits access in curved lumens. A further limitation of stiff shafts is that they reduce the options for carrier instrument flexibility and maneuverability.

The closing force of a traditional forceps biopsy instrument is limited by a shaft length ranging from 100 cm to 220 cm and the multiple curves traversed within the endoscope that must conform to a lumen. Because of these disabilities, endoscopic biopsy forceps that are 5 to 9 French in diameter rip the mucosal biopsy from the muscularis mucosa. This gives a biopsy that is larger than the forceps cup and varies in size. Furthermore, tissue distortion from biopsy trauma makes histopathologic interpretation difficult because of crush and shear artifacts. These artifacts result in false positive and false negative histopathologic interpretations of biopsy specimens leading to an incorrect diagnosis.

U.S. Pat. Nos. 5,685,320 and 5,782,747, both to Zimmon, both of which are herein incorporated by reference, solve this problem by sharply cutting biopsies of defined size that are suitable for passage through the tube shaft to an external receptacle. In U.S. Pat. No. 5,685,320 to Zimmon, herein incorporated by reference, the lateral biopsy device uses a precise distance between the central actuator wire and the cutting blade to control biopsy depth. Consequently, biopsy depth is less than one half of the shaft diameter. Actuator wire movement that limits the length of the cutting notch controls biopsy length. Width of the tangential biopsy is less than one half the tube shaft radius. The cut biopsy is then captured within the tube shaft at the time of biopsy and therefore available to move into the collection cassette.

In U.S. Pat. No. 5,782,747, the spring based multi-purpose medical instrument compresses folded spring sharp biopsy cups by sliding the tube shaft over a folded spring. The actuator wire only serves to hold the folded spring blade in the biopsy position during biopsy cutting. The closed biopsy cups both cut and capture a biopsy of controlled size that is matched to the tube shaft and therefore available to move into the storage cassette.

The motive force of suction or fluid pressure propels the precisely cut biopsy from either device into the proximal collection cassette as described in U.S. Pat. No. 6,071,248 to Zimmon, which is herein incorporated by reference. In U.S. Pat. No. 6,322,522 to Zimmon, which is herein incorporated by reference, the spring based multi-purpose medical instrument is modified to capture biopsy specimens in a removable cassette or cassettes at the proximal end of the biopsy instrument for immediate processing and analysis without removing and destroying the biopsy instrument to form the cassette. This improvement allows real time specimen analysis during the biopsy procedure and the use of a relatively expensive reusable or reprocessable biopsy instrument.

The serial collection, storage and processing of multiple specimens within a biopsy instrument yields a great savings of time and effort in processing the biopsies, as well as preventing specimen loss or damage during handling and protecting staff from infectious material and toxic fixatives. This goal is facilitated by applying redundant methods for forcing the minute biopsy specimens into a storage cassette of the biopsy instrument and by minimizing the operating parts of the biopsy instrument to maximize the storage volume.

Although the prior art has made safe efficient biopsy deep within the patient possible, the need for additional improvements remains.

SUMMARY OF THE INVENTION

It is therefore an object of the present invention to provide a distal removable internal biopsy collection, storage and processing cassette that is simple to use and provides a convenient distal removable storage cassette for processing of the serial collected biopsy specimens when used with a 30 to 220 cm long flexible biopsy instrument 5 to 36 French (1.6 to 12 mm) in diameter.

In the spring based instrument the device according to the invention comprises a flexible plastic shaft with a relatively large central lumen. The distal end of the shaft contains a remotely controllable folded spring jaw biopsy device of the type previously described above within the shaft lumen, that is stabilized by guide grooves in the metal or plastic internal cassette that prevent twisting of the folded spring. The junction of the shaft tip and the spring jaw may be angulated to increase the distance between the jaws when they are extended. When extended, the folded spring jaw is biased in an open position.

To biopsy the extended biopsy cups are pushed into the tissue. The depth of biopsy is controlled by the size of the biopsy cups, the distance between the cups and the external edge of the tip tube that prevents further tissue penetration when it contacts the tissue surface. As the retracting cups pass the mouth of the tip tube and the biased arms of the folded spring enter the tube shaft they are forced closed to cut a biopsy of precise size. Travel of the cut biopsy into the tip tube of the storage cassette moves the biopsy past a holding pawl into the storage cassette. As the biased spring jaw reaches the pawl a slot in the tip tube allows the jaws to open releasing the biopsy specimen. Each subsequent biopsy traverses the same path to pack its predecessors into the storage cassette in order of acquisition.

After the specimens are collected, the cassette is removed by depressing the cassette locking pin. The cassette is capped. A perforated cassette allows processing of the specimens without further handling with the serial specimens enclosed in order of acquisition and ready for fixation and processing. After processing to wax, the cassette is opened and the biopsies are ready for slicing, still in order of acquisition. Thus, a single log prepared at the time of biopsy serves to identify each specimen to the submitter and laboratory, and for reporting without handling, risk of biopsy loss or documentation error.

This invention has the option for use without an endoscope through a second external bendable tube shaft. The external tube shaft may be plastic, metal or any bendable material. The operator forms and inserts the tube shaft into the biopsy site. A spring based biopsy instrument of chosen diameter and flexibility is passed through the outer shaft to perform a biopsy or other operation. Operation of this invention may be monitored radiologically, visually, by palpation or any alternative.

One embodiment of this improved design for serial collection storage and processing is to use the cassette as the site of fixation, processing, staining or tissue testing by loading it with the appropriate reagents. When the cassette is made of an appropriate material, slicing for slide mounting is performed through the cassette without removing the specimens. In another embodiment the storage cassette is used as the reaction chamber for almost in vivo chemical, biological or genetic testing by immediately exposure of the biopsy specimens to reagents before metabolic changes, degradation or contamination can occur. In another embodiment the storage cassette is transparent so that the biopsies are immediately available for inspection and analysis without handling. This embodiment avoids the risk of exposure to fixatives or infectious agents yet makes analysis of pristine unfixed specimens by spectroscopy or other physical methods immediately possible without risk of infection or contamination. In another embodiment the open tube shaft with a side arm is used for fluid sampling or injection for irrigation, injection of radiopaque contrast or tissue stains.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
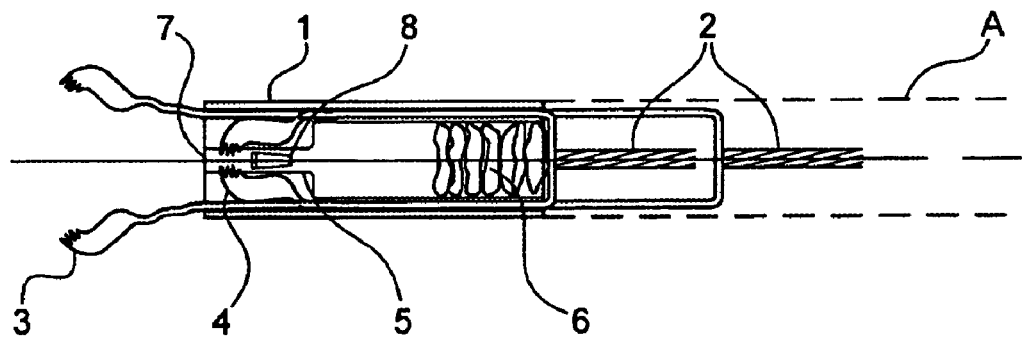
FIG. 1 shows a cross-sectional view of the device according to the invention in an open position.

For purposes of promoting an understanding of the principles of the invention reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
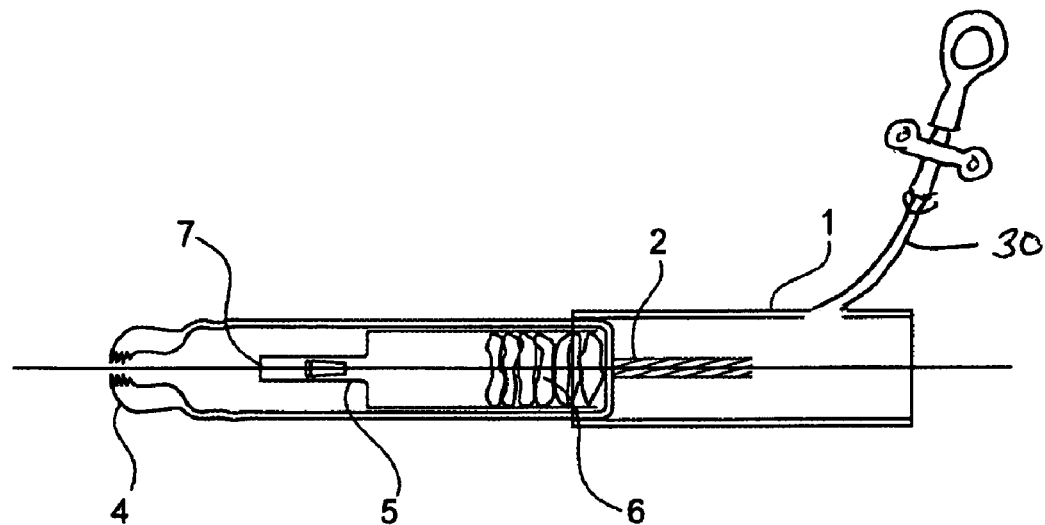
FIG. 2 shows a cross-sectional view of the device according to the invention in a closed position.

FIGS. 1 and 2 show the device according to the invention, which retrieves specimens 6 through a spring-based biopsy cutting tool 3. Cutting tool 3 is connected to the central actuator wire arranged inside a catheter tip tube 1, which has two short side slots and a large central lumen. The tip tube is removably connected to the longer tube shaft (A) containing the actuator wire that extends proximally to the handle. A side arm (not shown) that connects to the central lumen of the tube shaft is arranged proximally near the handle. The tip tube lumen contains the cassette 5 which acts as a specimen holding chamber, as shown in FIG. 2. The cassette can be made of any suitable material such as metal or plastic. Guide slots in the cassette prevent twisting of the folded spring jaw arms that are held in place by the tip tube. Cutting tool 3 has two spring-based jaws 4 equipped with two open-faced cutting blades on each jaw of cutting tool 3. The cassette locking pin 7 holds the cassette in place until removal.

In FIG. 1, the cutting tool 3 is deployed to cut and retrieve biopsy specimens, and to bring the specimens inside cassette 5 for storage. The movement of the tool is controlled by pulling the actuator wire 2, which causes the tool to retract (FIG. 2) encountering the edges of the tip tube causing the retracted jaws 4 to come together to cut specimen 6. Further pulling on wire 2 causes the cutting tool to retract inside the tube tip 1 lumen, where the folded spring jaw arms enter the slot in the tip tube to open the jaws as the specimen passes the pawl and pull specimen 6 inside the cassette 5. Alternatively, the tube shaft is advanced over the spring jaws while holding the actuator wire in place, forcing the jaws closed to cut the biopsy. After specimen 6 is deposited inside cassette 5 the tool 4 can then be deployed to cut and retrieve additional specimens. The holding pawl 8 traps each specimen inside the cassette 5. As the biopsy procedure is repeated each preceding specimen is packed deeper into the cassette 6.

Figure 3:
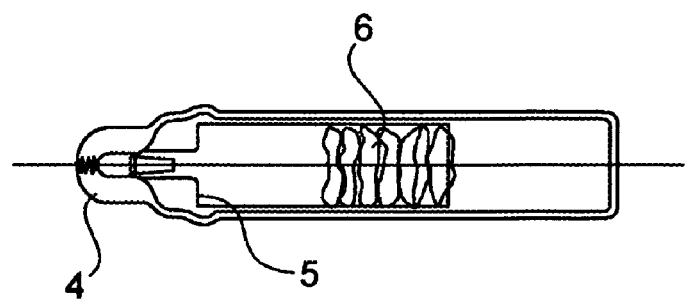
FIG. 3 shows the cutting cups and cassette after removal of the actuator wire.

FIG. 3 shows the cutting cups and cassette after removal of the actuator wire.

Figure 4:
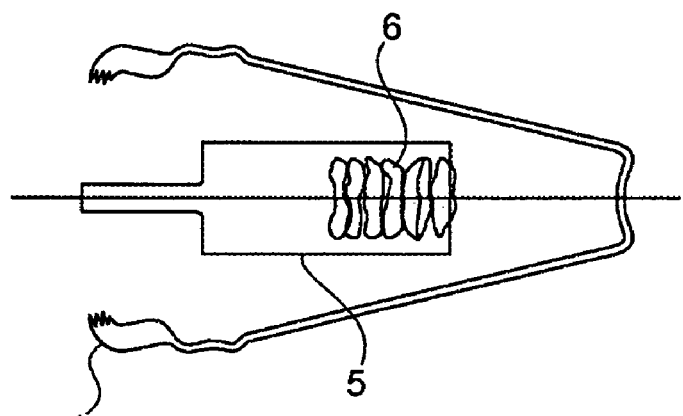
FIG. 4 shows the storage cassette and cutting tool removed from the tube shaft.

FIG. 4 shows the storage cassette and cutting tool removed from the tip tube shaft.

Figure 5:
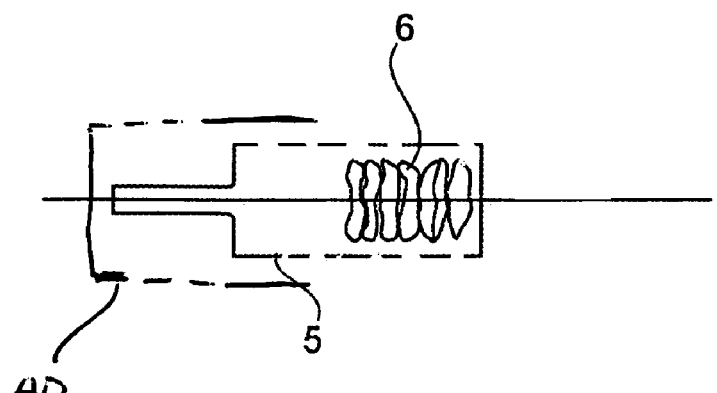
FIG. 5 shows the storage cassette after removal of the cutting tool.

FIG. 5 shows the storage cassette after removal of the cutting tool.

The operation of the serial collection forceps according to the invention is as follows:

The Tip Tube 1 is connected to an outer flexible sheath (A) which, in turn is connected to the handle. The control wire 2 slides down the center of the outer sheath and is axially moved by the handle Cutting tool 3 is pushed out of or pulled into the tip tube 1 by control wire 2. When moved out of tip tube 1, the jaws 4 separate under spring bias. To take a tissue biopsy, the forceps with open, Cutting tool 3 is pushed into the tissue and then the jaws are retracted back into the tip tube 1. As the jaws 4 pass the mouth of tip tube 1, the jaws are forced closed. When the jaws 4 close they take a bite of the tissue in which they were embedded. The continued travel of jaws 4 into tip tube 1 moves the tissue sample past holding pawl 8 and into the front of cassette 5. As the jaws 4 are extended for additional tissue samples, the existing tissue sample is detained by holding pawl 8. Another tissue sample is harvested in the aforementioned manor. While the jaws are being retracted past holding pawl 8, they encounter the previously harvested sample, pushing it further rearward into the cassette 5. As additional tissue samples are harvested, they continue pushing the previously harvested samples toward the back of the cassette 5, thus stacking them in serial order 6 for later examination and identification.

When the required quantity of tissue samples 6 has been harvested, the cassette 5 can be removed from tip tube 1 by depressing the cassette locking pin 7 and simultaneously operating control wire 2 toward the distal end of the device. The distal traveling jaws will push cassette 5 out of tip tube 1 and allow the filled cassette 5 to be removed and prepared for transport to the laboratory.

In a preferred embodiment as shown in FIG. 2, side arm 30 attached to the tube shaft 1 is used for fluid sampling or injection for irrigation, injection of radiopaque contrast or tissue stains before or after biopsy. Biopsy instrument spraying of methylene blue, Lugols iodine, indigo carmine or other stains prior to biopsy obviates the need to use a dedicated spray catheter spray that requires removal of the biopsy instrument followed by passage and removal of the spray catheter prior to biopsy at each site of interest.

In a preferred embodiment, when the desired specimens 6 have been collected, tip tube 1 is removed from catheter A and the end is capped with a perforated cap 40. Fixatives or reagents can be injected through cap 40. A perforated cassette (not shown) containing biopsies is placed in fixative for processing in order of acquisition without the preparation of additional logs or handling.

In a preferred embodiment, the biopsy instrument is reusable after the initial serial collection, storage and processing cassette is removed. Additional tip tubes 1 and cassettes 5 can then be connected to the actuator wire 2 for the harvesting of additional biopsies 6. This obviates the need and expense of using more than one biopsy instrument per patient when the first processing cassette is full. Furthermore separate specimens can be obtained in individual cassettes for inspection, physical analysis, fixation, refrigeration, chemical, biological, or genetic analysis or for frozen section or fixed histopathologic analysis. This is advantageous since each type of analysis requires different handling.

In a preferred embodiment, multiple cassettes 5 in tip tubes 1 containing different fixatives or reagents are used to perform multiple and immediate almost in vivo testing of biopsy specimens. A variety of cassettes and cassette functions can be provided. The commonly used dip stick chemical or biological assays can easily be incorporated into a transparent removable cassette for immediate detection of abnormalities such as infection, dysplasia or neoplasia. An example is the testing of biopsies for *H. pylori* where currently the fresh potentially infectious biopsy specimen is removed from the biopsy instrument and placed in a vessel containing reagents to detect the enzyme urease. If the test were performed in a cassette, positive biopsies could be submitted to microscopic examination for confirmation. If negative, additional biopsies could be taken to confirm the diagnosis. A complex physical analysis such as endoscopic laser reflectance spectroscopy followed by biopsy would be replaced by biopsy with external reflectance spectroscopy of biopsies in the cassette. The laser spectroscopy endoscope apparatus is replaced by external spectroscopy and the biopsies immediately available for chemical, biological, enzymatic, histopathologic and other analysis. These improvements reduce procedure time with the patient under anesthesia, limit handling of potentially infectious tissue by staff, speed diagnosis and reduce cost. With reagents in the biopsy storage cassette handling is obviated and test results are immediately available to the operator.

In a preferred embodiment, the biopsy instrument 1 with distal tip tube removed can be washed, disinfected and reused. Consequently a more expensive, more efficient reusable biopsy instrument could replace a disposable instrument at less cost and the advantages of serial collection, storage and processing with multiple distal reusable cassettes retained.

In contrast to the present invention, most current biopsy instruments must be removed from the endoscope to retrieve the specimen and begin processing after each or at most a few biopsies are taken. This action is often accompanied by endoscope movement that may require repositioning of the endoscope or even loss of position rendering additional biopsies impossible. These delays prolong the procedure and period of anesthesia. The risk of complications and cost is thereby increased.

In the pathology laboratory it is difficult orient free floating minute biopsy specimens for wax embedding, sectioning and microscopic study. Time and effort are spent in biopsy orientation. A poorly oriented biopsy may obscure or yield a false diagnosis. A false negative diagnosis may force another procedure. A false positive diagnosis may precipitate unnecessary treatment. The pathologist may equivocate when interpreting a biopsy because of these well known problems. The distal removable storage cassette solves these problems by orienting the biopsy within the cassette. An external cassette lumen 1.5 wide by 24 mm deep holds 24 biopsies 1.5 mm wide, 1.5 mm long and 1 mm deep oriented in the cassette.

Accordingly, while only a few embodiments of the present invention have been shown and described, it is obvious that many changes and modifications may be made thereunto without departing from the spirit and scope of the invention.

What is claimed is:

1. An apparatus for performing a medical procedure, comprising:
    an elongated flexible member having an aperture extending longitudinally therethrough, said member having a proximal end and an opposite distal end;
    an actuator positioned within the aperture, said actuator having a proximal end and an opposite distal end;
    a side arm connected to the flexible member and communicating with said aperture for fluid sampling, irrigation, and injection of radiopaque contrast or tissue stains;
    a biopsy device connected to the distal end of the actuator and located at the distal end of the flexible member for cutting and collecting biopsy specimens of controlled size, said biopsy device retracting into said flexible member before and after biopsy;
    a distal storage and collection cassette removably held within the aperture of said elongated flexible member at the distal end of the flexible member for receiving biopsy specimens cut and collected by the biopsy device, wherein said cassette has an internal adhesive surface to adhere a cut or mucosal biopsy surface and thereby orient collected biopsy specimens in said cassette and wherein said cassette is in fluid communication with said aperture;
    means for sealing the removable distal storage and collection cassette before use or when said cassette has been separated from the flexible member for storage and processing of biopsy specimens collected by the biopsy device in the order of collection;
    wherein the distal storage and collection cassette incorporates a means for chemical, biological or genetic analysis by reacting with the biopsy specimens before metabolic changes, degradation or contamination can occur;
    wherein the side arm communicates with the biopsy device and said cassette for irrigation and cleansing of said biopsy device and cassette prior to and during biopsy for removing contaminants from the biopsy device and cassette; and
    wherein the cassette is disposed immediately adjacent the biopsy device to maintain the specimens serially in the order of acquisition, and wherein the cassette is smaller in diameter than the biopsy device; and
    wherein the distal storage and collection cassette is perforated to allow entrance of fixative or other reagents via injection from the side arm without handling.

2. The apparatus of claim 1, wherein the biopsy device comprises a spring jaw having a cutting tool, said spring jaw being remotely deployable from said flexible member, and an internal jaw guide in the distal end of said member, said jaw guide controlling the precise movement of said jaw and said jaw forcing the biopsy specimen into a distal storage and collection cassette cavity, and said jaw to provide a defined biopsy size.

3. The apparatus of claim 1, wherein said cassette incorporates tissue fixative or stain for immediate reaction with the collected specimens.

4. The apparatus according to claim 1, wherein multiple cassettes of similar or differing usages may be connected to the flexible member, said multiple cassettes being made of different materials from each other, and at least one of said cassettes being sliceable.

5. The apparatus according to claim 1, wherein the flexible member is disposable or reusable after washing and disinfecting by connecting to a new tip tube containing a storage cassette.

6. The apparatus of claim 1, wherein the sealing means is a cap positionable over said cassette before use or when said cassette is separated from the flexible member.

7. The apparatus of claim 6, wherein the cap is perforated.

8. An apparatus for performing a medical procedure, comprising:
    an elongated flexible member having an aperture extending longitudinally therethrough, said member having a proximal end and an opposite distal end;
    an actuator positioned within the aperture, said actuator having a proximal end and an opposite distal end;
    a side arm connected to the flexible member and communicating with said aperture for fluid sampling, irrigation, and injection of radiopaque contrast or tissue stains;
    a biopsy device connected to the distal end of the actuator and located at the distal end of the flexible member for cutting and collecting biopsy specimens of controlled size, said biopsy device retracting into said flexible member before and after biopsy;
    a storage and collection cassette removably held within the aperture of said elongated flexible member at the distal end of the flexible member for receiving biopsy specimens cut and collected by the biopsy means device, wherein said cassette has an internal adhesive surface to adhere a cut or mucosal biopsy surface and thereby orient collected biopsy specimens in said cassette and wherein said cassette is in fluid communication with said aperture;
    means for sealing the removable storage and collection cassette before use or when said cassette has been separated from the flexible member for storage and processing of biopsy specimens collected by the biopsy device in the order of collection;
    wherein the storage and collection cassette is translucent for visual inspection or spectrometry;
    wherein the side arm communicates with the biopsy device and said cassette for irrigation and cleansing of said biopsy device and cassette prior to and during biopsy for removing contaminants from the biopsy device and cassette; and wherein the storage and collection cassette is disposed immediately adjacent the biopsy device to maintain the specimens serially in the order of acquisition, and wherein said cassette is smaller in diameter than the biopsy device; and wherein the distal storage and collection cassette is perforated to allow entrance of fixative or other reagents via injection from the side arm without handling.

* * * * *